US005766232A

United States Patent [19]

Grevious et al.

[11] Patent Number: 5,766,232
[45] Date of Patent: Jun. 16, 1998

[54] METHOD AND APPARATUS FOR ALTERING THE Q OF AN IMPLANTABLE MEDICAL DEVICE TELEMETRY ANTENNA

[75] Inventors: John J. Grevious, Minneapolis, Minn.; Anne J. C. J. van Leeuwen, Apeldoorn, Netherlands; Mark W. Sandberg, Coon Rapids; Kenneth L. Graves, Golden Valley, both of Minn.

[73] Assignee: Medtronic, Inc., Minneapolis, Minn.

[21] Appl. No.: 813,963

[22] Filed: Mar. 3, 1997

Related U.S. Application Data

[60] Provisional application No. 60/017,236 May 10, 1996.
[51] Int. Cl.⁶ .................................................. A61N 1/08
[52] U.S. Cl. .............................. 607/60; 607/30; 607/32
[58] Field of Search .............................. 607/30, 31, 32, 607/60; 128/903

[56] References Cited

U.S. PATENT DOCUMENTS

| | | | |
|---|---|---|---|
| 4,006,086 | 2/1977 | Tsunoi | 210/242 R |
| 4,124,031 | 11/1978 | Mensink et al. | 128/419 PG |
| 4,304,237 | 12/1981 | Mensink | 128/419 |
| 4,550,370 | 10/1985 | Baker | 364/413 |
| 4,556,063 | 12/1985 | Thompson et al. | 128/419 PT |
| 4,571,589 | 2/1986 | Slocum et al. | 340/870.32 |
| 5,117,825 | 6/1992 | Grevious | 128/419 PG |
| 5,127,404 | 7/1992 | Wyborny et al. | 128/419 PG |
| 5,168,871 | 12/1992 | Grevious | 128/419 PT |
| 5,292,243 | 3/1994 | Blanchette et al. | 607/32 |
| 5,342,315 | 8/1994 | Rowe et al. | 604/167 |
| 5,354,319 | 10/1994 | Wyborny et al. | 607/32 |
| 5,562,714 | 10/1996 | Grevious | 607/32 |

*Primary Examiner*—William E. Kamm
*Assistant Examiner*—Kennedy J. Schaetzle
*Attorney, Agent, or Firm*—Thomas F. Woods; Harold R. Patton

[57] ABSTRACT

A method and apparatus for programming implantable medical devices employing RF telemetry, and more particularly, altering the RF telemetry antenna Q to accommodate telemetry with implantable medical devices having differing RF telemetry receiving characteristics is disclosed. The RF head telemetry antenna comprises an LC tank circuit including an RF head telemetry coil and a tuning capacitor and has a predetermined antenna Q. The RF head telemetry antenna is adapted to be driven into oscillation by applied oscillating energy and to continue to oscillate in a series of declining amplitude oscillations after the oscillating energy is no longer applied as residually stored oscillating energy is dissipated therethrough. A transmit telemetry pulse is generated for establishing a pulse width of the telemetry RF pulse. Upon the termination of the telemetry transmit pulse antenna Q is reduced from the predetermined antenna Q, and the declining amplitude oscillations are thereby attenuated. The reduction of the antenna Q is effected by a grounding a sense coil located in the programmer RF head that is employed to sense the RF pulse and regulate the amplitude thereof during the transmit telemetry pulse at the termination of the transmit telemetry pulse.

20 Claims, 6 Drawing Sheets

METHOD AND APPARATUS FOR ALTERING THE Q OF AN IMPLANTABLE MEDICAL DEVICE TELEMETRY ANTENNA

This application claims the benefit of U.S. Provisional Application Ser. No. 60/017,236, filed May 10, 1996, entitled . METHOD AND APPARATUS FOR MAGNETIC FIELD LOAD CONTROL in the names of J. Grevious et al.

CROSS-REFERENCE TO RELATED APPLICATIONS

Reference is hereby made to commonly assigned, co-pending U.S. Pat. application Ser. Nos. 08/584,851 filed Jan. 11,1996, for ADAPTIVE PERFORMANCE-OPTIMIZING COMMUNICATION SYSTEM FOR COMMUNICATING WITH AN IMPLANTED MEDICAL DEVICE in the names of S. Goedeke et al. now U.S. Pat. No. 5,683,432; 08/768,605 filed Dec. 18,1996, for IMPLANTABLE DEVICE TELEMETRY HIGH DATA TRANSMISSION RATE TELEMETRY TRANSMISSION FORMAT FOR IMPLANTED MEDICAL DEVICE in the names of J. Grevious et al.; and 08/842,581 filed Apr. 15, 1997 for HIGH DATA TRANSMISSION RATE TELEMETRY TRANSMISSION FORMAT FOR IMPLANTED MEDICAL DEVICE in the names of J. Grevious et al.

BACKGROUND OF THE INVENTION

1. Field of the Invention

The present invention generally relates to the programming of programmable implantable medical devices employing RF telemetry, and more particularly, pertains to the alteration of the RF telemetry antenna Q to accommodate telemetry with implantable medical devices having differing RF telemetry receiving characteristics.

2. Description of the Prior Art

The earliest implantable medical devices, e.g., implantable cardiac pacemakers, were designed to operate in a typically single operating mode governed by fixed operating parameters without any ability to change the operating mode or otherwise communicate percutaneously with external equipment. In time, it became apparent that it would be clinically desirable to vary certain of the operating parameters and/or modes of operation. An initial approach employed with implanted cardiac pacemakers involved use of miniature rheostats that could be directly accessed by a needle-like tool inserted through the patient's skin to adjust a resistance in the pacing rate or pulse width setting circuit. Later, miniaturized reed switches were incorporated into the pacing rate or pulse width circuits that responded to magnetic fields applied through the skin by an external magnet placed over the implant site. The pulse width, pacing rate and a limited number of pacing modes could be adjusted in this manner.

It was also realized that the operation of an implantable cardiac pacemaker could be observed, for example, by use of a standard ECG machine and timing of intervals between pacing pulse spikes in the ECG tracing recorded from skin electrodes on the patient. Later, it became known that this technique could be used to detect data sent from the implanted cardiac pacemaker by modulating the pacing pulse amplitude, width or frequency in some manner. This approach could only provide a low bandpass data channel, of course, to avoid interfering with the primary function of pacing the patient's heart when necessary. One use of this technique was to monitor impending battery depletion through observation of a change in the pacing rate from a preset or programmed pacing rate in response to battery depletion.

As digital circuit technology advanced, it was recognized that control of operating modes and parameters of implanted medical devices could be realized in digital or binary circuits employing memorized control states or operating parameter values. In order to change an operating mode or parameter value, "programmers" were developed based on radio frequency (RF) downlink data communication from an external programmer transceiver to a telemetry transceiver and memory incorporated within the implantable pacemaker pulse generator. The operating modes and parameters that may be programmed are only limited by the designed capabilities of the implanted device.

It also became possible to provide uplink data telemetry to transmit the contents of a register or memory within the implanted pacemaker pulse generator to the telemetry receiver within the programmer employing the same RF transmission capabilities. Today, both analog and digital information or data can be transmitted by uplink RF telemetry from the implanted device to the external programmer. The analog information has typically included battery voltage, sampled intracardiac electrocardiogram amplitude values, sensor output signals, pacing pulse amplitude, energy, and pulse width, and pacing lead impedance. The digital information typically includes, statistics related to performance, event markers, current values of programmable parameters, implant data, and patient and pulse generator identifier codes. Similar analog and digital data is telemetered from implanted cardiac monitors, drug dispensers, cardioverter/defibrillators, and pacemaker/cardioverter/defibrillators.

Many types of RF telemetry systems have been or currently are used in connection with implantable medical devices, such as cardiac pacemaker pulse generators. An example of a pulse interval modulation (PIM) telemetry system used for transmitting analog and digital data, individually and serially, from an implanted pacemaker to a remote programmer is disclosed in U.S. Pat. No. 4,556,063 issued to Thompson et al., incorporated herein by reference. A further example of a pacemaker programmer for use with programmable cardiac pacemakers having RF telemetry capabilities is disclosed in U.S. Pat. No. 4,550,370, issued to Baker, incorporated herein by reference. A further example of a pulse width modulation (PWM) telemetry system for transmitting binary "1" and "0" encoded RF pulse widths from an implanted cardiac pacemaker to an external programmer is described in U.S. Pat. No. 4,571,589, issued to Slocum et al., incorporated herein by reference.

An extensive description of the historical development of uplink and downlink telemetry transmission formats and is set forth in the above-referenced '851 application and in the following series of commonly assigned patents all of which are incorporated herein by reference in their entireties. Commonly assigned U.S. Pat. No. 5,127,404 to Grevious et al. sets forth an improved method of frame based, pulse position modulated (PPM) of data particularly for uplink telemetry. The frame-based PPM telemetry format increases bandwidth well above simple PIM or pulse width modulation (PWM) binary bit stream transmissions and thereby conserves energy of the implanted medical device. Commonly assigned U.S. Pat. No. 5,168,871 to Grevious et al. sets forth an improvement in the telemetry system of the '404 patent for detecting uplink telemetry RF pulse bursts that are corrupted in a noisy environment. Commonly assigned U.S. Pat. No. 5,292,343 to Blanchette et al. sets forth a further improvement in the telemetry system of the '404 patent employing a hand shake protocol for maintaining the communications link between the external programmer and the implanted medical device despite instability in the programmer RF head. Commonly assigned U.S. Pat. No. 5,324,315 to Grevious sets forth an improvement in the uplink telemetry system of the '404 patent for providing feedback to the programmer to aid in optimally positioning the programmer RF head over the implanted medical device. Commonly assigned U.S. Pat. No. 5,117,825 to Grevious sets forth an further improvement in the programmer RF head for regulating the output level of the magnetic, H field of the RF head telemetry antenna using a signal induced in a sense coil in a feedback loop to control gain of an amplifier driving the RF head telemetry antenna. Commonly assigned U.S. Pat. No. 5,562,714 to Grevious sets forth a further solution to the regulation of the output level of the magnetic, H field generated by the RF head telemetry antenna using the sense coil current to directly load the H field. Commonly assigned U.S. Pat. No. 5,354,319 to Wyborney et al. sets forth a number of further improvements in the frame based telemetry system of the '404 patent. Many of these improvements are incorporated into MEDTRONIC® Model 9760, 9766 and 9790 programmers.

The downlink telemetry RF pulse bursts generated in these frame based, MEDTRONIC® telemetry systems are relatively constant in frequency and pulse width due to the characteristics of the programmer RF head telemetry antenna and the frequency at which it is driven. A fixed interval telemetry transmit telemetry (XMITTLM) pulse is applied to the programmer telemetry transmitter circuit which drives an oscillating signal into the RF head telemetry antenna comprising a coil or coils having an inductance L and a capacitor or capacitors having a capacitance C. The antenna LC circuit is tuned in its connection with a receiver circuit to resonate in response to a transient signal (e.g. spurious noise) at about 128 kHz. However, an uplink 175 kHz signal can be detected. During downlink telemetry, the antenna LC tank circuit resonates and generates a burst of RF cycles at the downlink 175 kHz frequency, as described in the above-incorporated '714 and '871 patents. At the termination of the telemetry transmit pulse, the LC tank circuit continues to resonate as stored energy is dissipated, resulting in a series of declining amplitude, damped sinusoidal waves to a quiescent level.

The programmer RF head also includes other components than the LC antenna circuit, notably a toroidal shaped permanent magnet for closing a magnetic field sensitive switch in the implanted medical device when the RF head is held over it during telemetry transmission or other operations and the above-referenced sense coil. The sense coil is used during downlink telemetry to verify that an RF pulse is being transmitted and to regulate the amplitude of the H field as described in the above-incorporated '714 patent. The RF head telemetry antenna and associated mechanical components in the RF programmer RF head of such MEDTRONIC® programmers are designed to minimize antenna loading to achieve the highest possible antenna Q. This requires special configurations of a non-conductive or segmented magnet (used to close a reed switch in the implanted medical device), antenna coil, sense coil and segmented E-shields and attention to loading by other components, e.g. the printed wiring board circuits. The resulting H field that is generated during the ringing of the antenna LC circuit is regulated in amplitude by loading effected when voltage induced in the sense coil causes breakdown diodes to conduct. This passive circuit regulates the Q by direct loading of the H field when the diodes conduct as described in the above-incorporated '714 patent.

The downlink telemetry RF pulse exhibits a relatively rapid rise in amplitude in response to a XMITTLM pulse and is readily detected by an amplitude comparitor in the implanted medical device receiver. However, at the end of the XMITTLM pulse, the RF carrier frequency cycles fall off in amplitude at a slower rate. This is not a problem with MEDTRONIC® IPGs that respond to large amplitude, relatively long pulse width, downlink RF telemetry pulses.

However, not all manufacturers of programmable implanted medical devices and programmers employ a relatively high amplitude, carrier frequency burst as the RF pulse. For example, Vitatron Medical, B.V., a subsidiary of Medtronic, Inc., employs a fundamentally different LC antenna circuit design in its programmer RF heads that has a low to moderate Q and resulting H field and responds best to a single constant polarity, narrow pulse of relatively low amplitude.

The VITATRON® programming system and format developed historically from use of an intermittently applied, steady magnetic field as described in commonly assigned U.S. Pat. Nos. 4,124,031 and 4,304,237 to Mensick et al. Presently, the Vitatron® telemetry format requires that the received telemetry RF pulse have no more than three full sinusoidal transitions (or ring cycles) exceeding a voltage amplitude threshold. If the RF pulse is longer, it will be rejected as representing noise, and the telemetered data may be corrupted or required to be sent again in its entirety. The RF pulse is developed in an LC circuit that rings at a carrier frequency of approximately 40 kHz. The ideal RF pulse used in the VITATRON system would be a single biphasic transition of the carrier frequency.

The particular design of the VITATRON® programmer RF head takes this and other design requirements into account and uses the mechanical design of non-segmented E-shields and aluminum shielding plates oriented with respect to the RF head antenna coil to produce a desired amount of loading and a relatively low Q. As a result, antenna ringing is kept within the three ring limit, and the amplitude of the H field is lower than that produced by the MEDTRONIC® programmer RF head antenna coil.

At present, a wide variety of implanted medical devices are commercially released or proposed for clinical implantation including implantable cardiac pacemakers as well as implantable cardioverter-defibrillators, pacemaker-cardioverter-defibrillators, drug delivery pumps, cardiomyostimulators, cardiac and other physiologic monitors, nerve and muscle stimulators, deep brain stimulators, cochlear implants, artificial hearts, etc. The programming formats differ from manufacturer to manufacturer and sometimes between devices of differing types offered by the same manufacturer. Considerable effort has been expended by manufacturers over the years to ensure at least that current programmers operate with a wide range of both current and predecessor implanted medical devices offered by that manufacturer. It would be desirable to provide a greater range of use of programmers with implanted medical devices of related or unrelated manufacturers to simplify the programming of a wide range of such implanted medical devices.

Moreover, it has been proposed that the above-described, frame-based PPM telemetry format be employed for downlink telemetry transmissions as well as uplink telemetry transmissions. To implement that format into downlink telemetry transmissions, it would be necessary to substantially reduce the width of the transmitted RF pulses from the current pulse width to fit within the frame clock cycle that defines frame positions in each range of the frame. In such a case, it is proposed that the signal level on the implanted medical device telemetry antenna be sampled by a telemetry clock, e.g., a 32 kHz clock. Upon detection of each RF pulse, the receiver times the intervals between the RF pulses to first determine the start of each frame and then determine the information or commands in the frame in terms of successive clock cycles. The frame based, PPM telemetry system disclosed in the above-incorporated, commonly assigned patents increases the data transmission rate significantly over the simple bit stream telemetry transmission schemes using either PWM or PPM or PIM to distinguish a "1" from a "0". A great deal of data may be encoded in a single frame and transmitted within the frame period defined by a discrete number of telemetry clock cycles, thereby decreasing the required transmission time and diminishing battery current consumption.

However, the LC time constant and prolonged ringing of the RF pulse does limit the telemetry clock frequency that is used to define the frame pulse positions in the transmission mode and used to identify the pulse position in the receiving mode. For example, if a 32 kHz frame clock is used to format a frame having 64 positions, then the amplitude of the cycles constituting a single 175 kHz RF pulse must decrease below the detection threshold before the end of the 32 kHz clock period. Otherwise, confusion would arise as to which detected successive pulse position is correct.

As time passes, implanted medical devices become ever more complex in possible programmable operating modes, menus of available operating parameters, and capabilities of monitoring increasing varieties of physiologic conditions and electrical signals which place ever increasing demands on the programming system. It remains desirable to minimize the time spent in telemetry uplink and downlink transmissions both to reduce the likelihood that the telemetry link may be broken and to reduce current consumption. Consequently, a need remains for increasing the data transmission rate during downlink telemetry. As will become apparent from the following, the present invention satisfies that need as well.

SUMMARY OF THE INVENTION

It is an object of the present invention to solve these problems identified with prior art RF telemetry systems including the transmission rate limitations and the inability of a single RF pulse transmission programmer head to operate at high Q and moderate to low Q. It is therefore a further object of the present invention to simplify the requirements of programming implanted medical devices using a common programmer system that accounts for differences in the characteristics of the RF pulse. It is still a further object of the present invention to selectively tailor the downlink RF pulse characteristics to accommodate detection requirements or limitations of a variety of programmer formats and systems. It is yet another object of the present invention to tailor the decaying sinusoidal, amplitude modulation envelope of a downlink RF pulse burst to accommodate any particular RF pulse detection criteria used in such RF telemetry systems. It is a further object of the present invention to control the RF head antenna Q in order to precisely limit the number of carrier frequency pulses generated in an RF pulse, thereby allowing for greater control of RF pulse transmission rates.

In comparison to the known programming systems, the present invention provides numerous advantages. The same RF head antenna can be employed as a high Q, RF antenna or effectively as a low Q, RF antenna. The diminution of the residual energy ringing of the RF head LC tank circuit allows for increasing the rate of downlink telemetry or otherwise accommodating a variety of transmission rates and formats. The attenuation of the residual, damped sinusoidal RF pulse cycles at the end of the transmit telemetry command pulse allows the tailoring of the RF pulse width to limit it to a single RF carrier cycle or a discrete number of RF carrier cycles.

The present invention therefore provides solutions to problems of the transmitting information-encoded, telemetry signals percutaneously between an implanted medical device and an external device as telemetry RF pulses. In the preferred embodiment of the invention, these solutions are provided by the RF head telemetry antenna having a predetermined antenna Q during generation of the RF pulse. The RF telemetry head LC tank circuit is adapted to be driven into oscillation by applied oscillating energy and to continue to oscillate in a series of declining amplitude oscillations after the oscillating energy is no longer applied as residually stored oscillating energy is dissipated therethrough. Upon the termination of the telemetry transmit pulse, the antenna Q is reduced from the predetermined antenna Q and thereby rapidly attenuating the declining amplitude oscillations. Through control of the time period that the LC tank circuit is driven into oscillation and the rapid attenuation a discrete number of constant amplitude, a discrete, controllable number of RF carrier frequency cycles are generated.

BRIEF DESCRIPTION OF THE DRAWINGS

These and other objects, advantages and features of the present invention will be appreciated to those of skill in the art as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS

A preferred embodiment of the present invention relates to use of the improved downlink telemetry RF pulse generator within an external programmer of the types described above to program or interrogate an implantable medical device, e.g. a cardiac pacemaker or pacemaker-cardioverter-defibrillator pulse generator. However, those of skill in the art will be readily able to adapt the teachings found herein to other implantable medical devices as summarized above. It will also be understood that the present invention may be applied to any downlink data or command transmission formats that employ PPM, PWM, PIM or other data encoding and decoding techniques.

Figure 1:
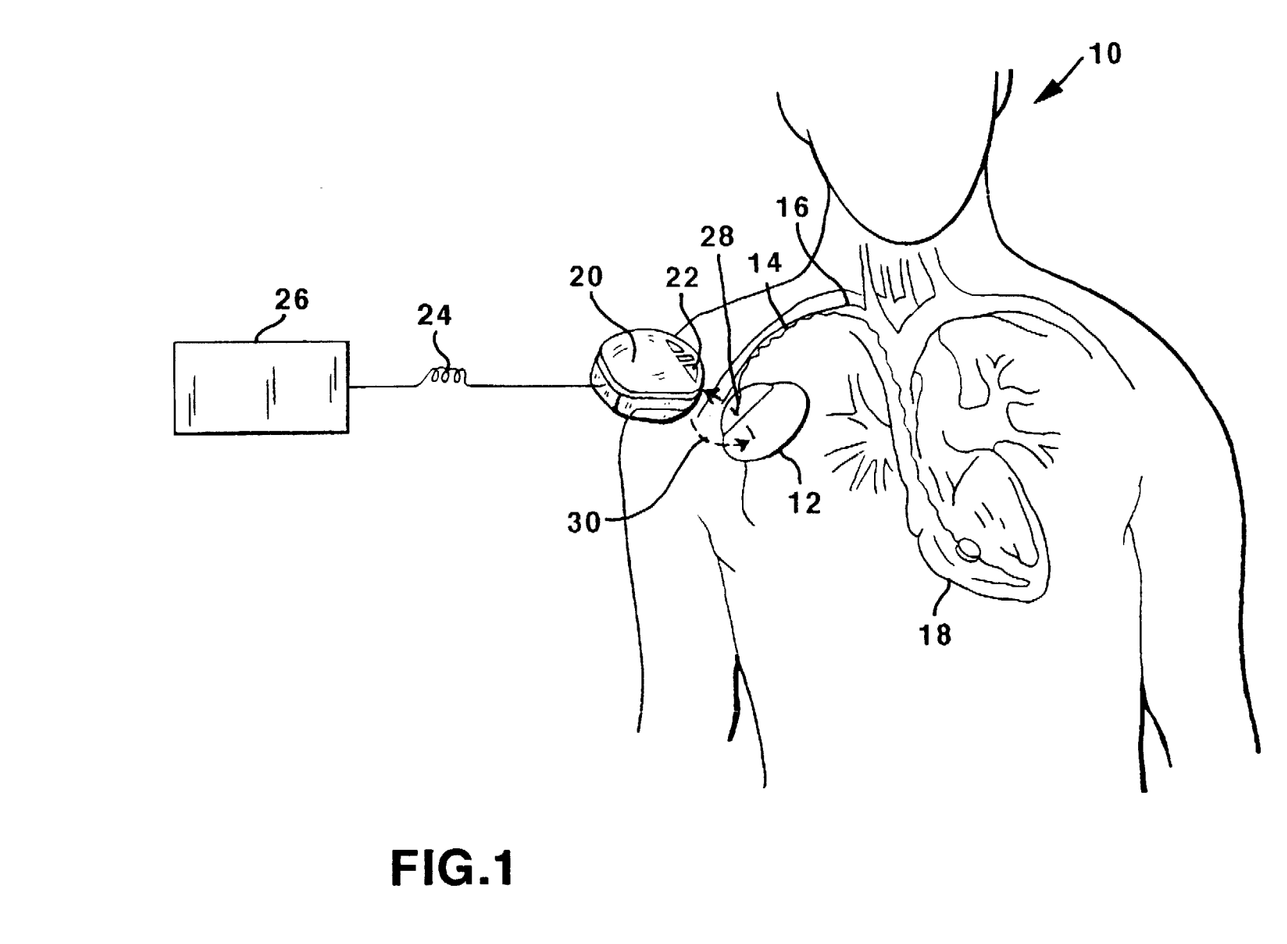
FIG. 1 is a simplified schematic view of an implantable medical device and external programmer embodying the improved programmer RF head and telemetry pulse generator in accordance with the present invention.

FIG. 1 is a simplified schematic diagram of the bi-directional telemetry communication between an external programmer 26 and an implanted medical device, e.g., a cardiac pacemaker implantable pulse generator (IPG) 12. The IPG 12 is implanted in the patient 10 beneath the patient's skin and typically oriented to the skin surface in the manner illustrated in the above-incorporated '714 patent. IPG 12 is electrically coupled to the heart 18 of the patient 10 through pace/sense electrodes and lead conductor(s) of at least one cardiac pacing lead 14 in a manner known in the art. The IPG 12 contains an operating system that may employ a microcomputer or a digital state machine for timing sensing and pacing functions in accordance with a programmed operating mode. The IPG 12 also contains sense amplifiers for detecting cardiac signals, patient activity sensors or other physiologic sensors for sensing the need for cardiac output, and pulse generating output circuits for delivering pacing pulses under control of the operating system in a manner well known in the prior art. The operating system includes memory registers or RAM for storing a variety of programmed-in operating mode and parameter values that are used by the operating system. The memory registers or RAM may also be used for storing data compiled from sensed cardiac activity and/or relating to operating history for telemetry out on receipt of a retrieval or interrogation instruction. Such an IPG 12 is described in detail in the above-referenced '581 application, incorporated by reference herein. All of these functions and operations are well known in the art, and many are employed in other programmable, implantable medical devices to store operating commands and data for controlling device operation and for later retrieval to diagnose device function or patient condition.

Programming commands or data are transmitted between an IPG telemetry antenna within IPG 12 and an RF head telemetry antenna within programmer RF head 20 during a telemetry uplink transmission 28 or downlink transmission 30. In a telemetry uplink transmission 28, the RF head telemetry antenna operates as a telemetry receiver antenna, and the IPG telemetry antenna operates as a telemetry transmitter antenna. Conversely, in a telemetry downlink transmission 30, the RF head telemetry antenna operates as a telemetry transmitter antenna, and the IPG telemetry antenna operates as a telemetry receiver antenna.

Figure 3:
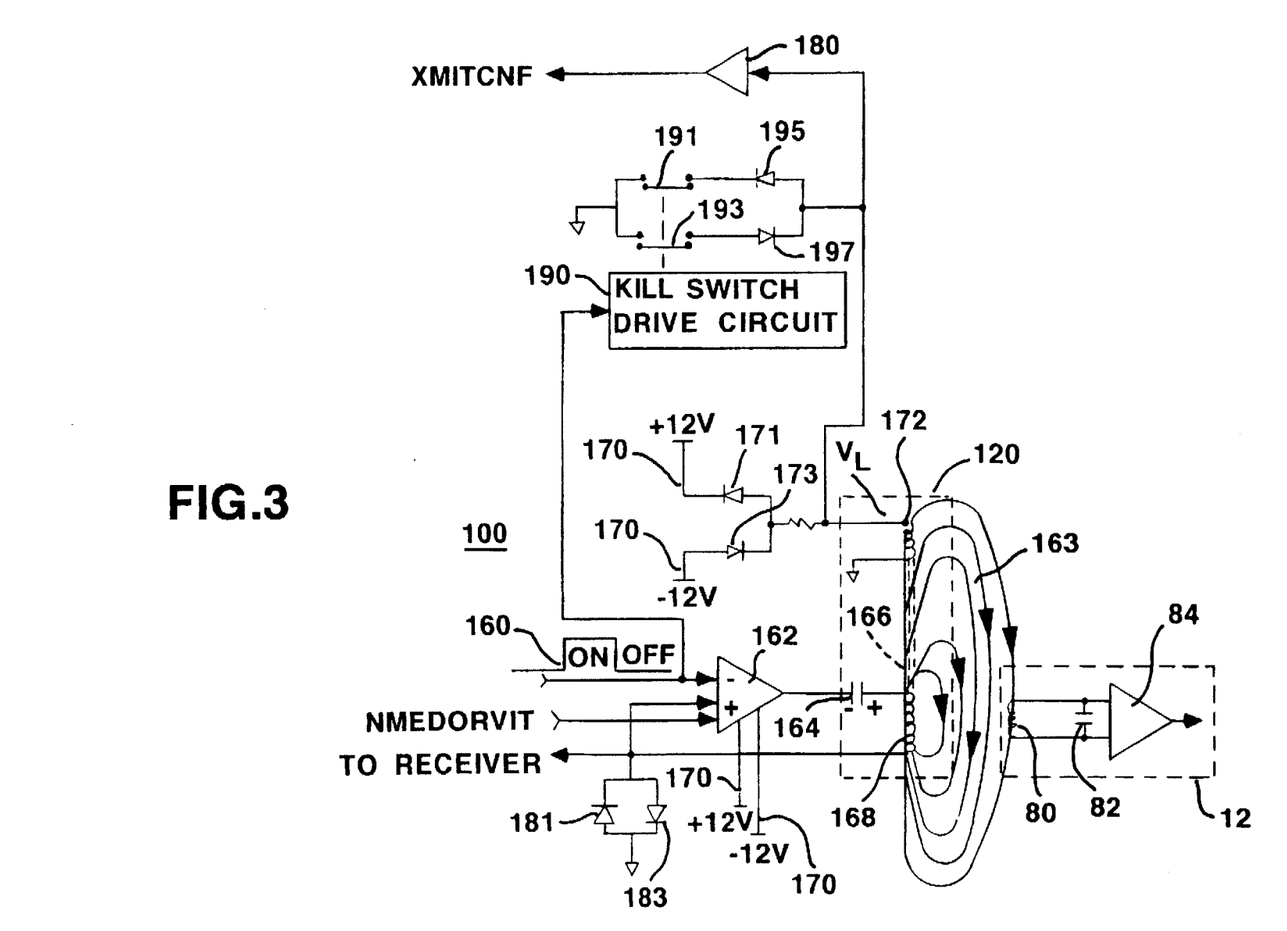
FIG. 3 is a simplified schematic diagram of the major components of the programmer RF head transmitter circuit employed in the system of FIGS. 1 and 2.
Figure 4:
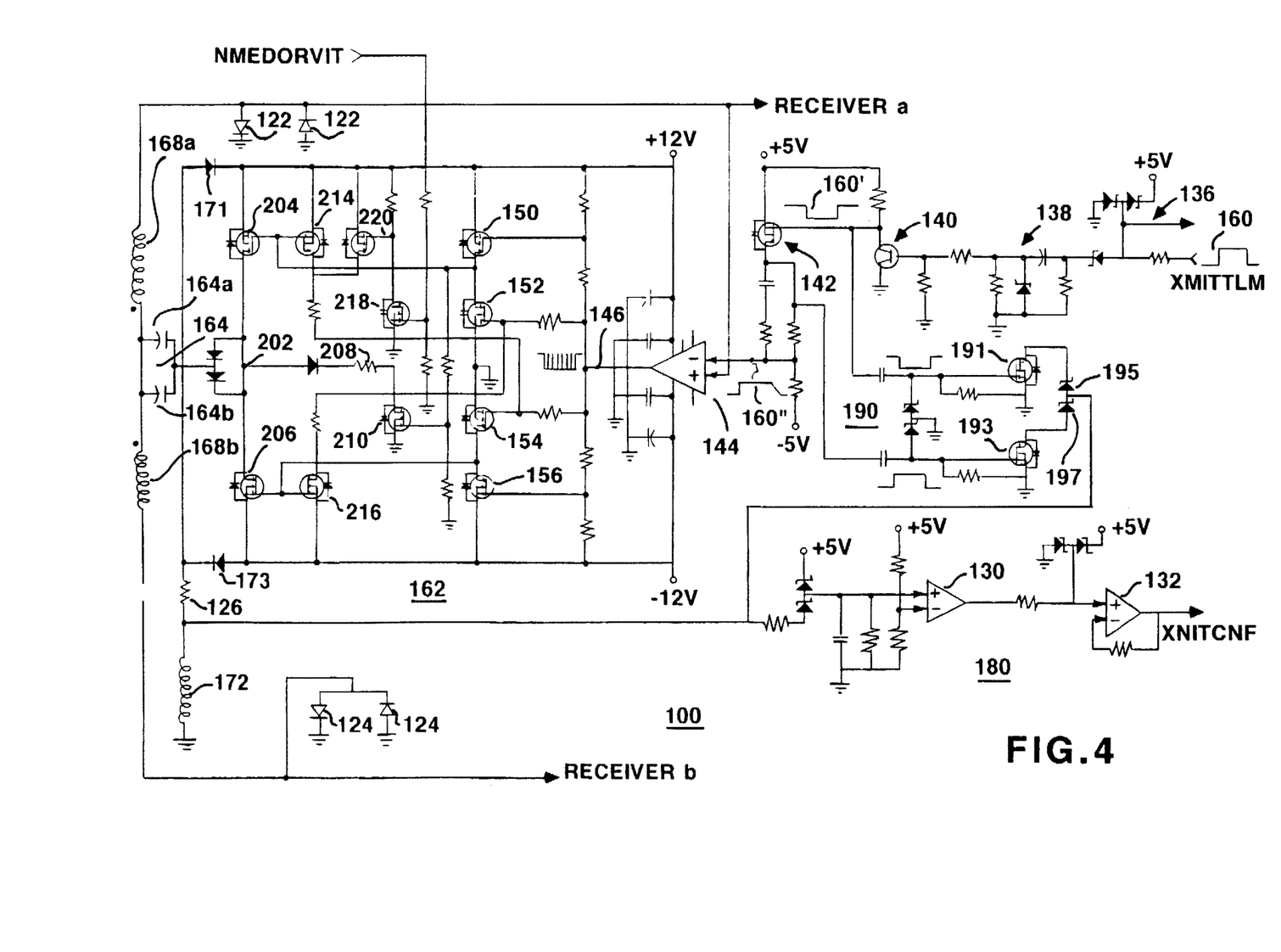
FIG. 4 is a detailed schematic diagram of the programmer RF head transmitter circuit of FIG. 3.

As illustrated in FIGS. 3 and 4 and described in greater detail below, each such telemetry antenna is formed of an antenna coil(s) having a coil(s) inductance L and a capacitor (s) having a capacitance C coupled together in an LC tank circuit configuration. Moreover, a sense coil illustrated in FIGS. 3 and 4 of the type described above is located in proximity to the RF head antenna LC circuit within programmer RF head 20. The LC tank circuit and the sense coil in the hand held, programmer RF head 20 are electrically connected to the external programmer 26 via an electrical cable 24. The programmer RF head 20 also may contain a toroidal permanent magnet which activates a reed switch in IPG 10 as a safety feature, as taught in U.S. Pat. No. 4,006,086 issued to Alferness et al., herein incorporated by reference. INTERROGATE and PROGRAM push-buttons and an LED display 22 are also provided on the programmer RF head 20 and are also electrically connected through electrical cable 24 to external programmer 26. The INTERROGATE and PROGRAM push-buttons are provided to be selectively depressed by the medical care giver to start the telemetry uplink and downlink transmissions 28 and 30, respectively, as described in detail in the above-incorporated '871 patent. The LED display is also provided that is coupled to a sense circuit in programmer 26 described above and is illuminated during a telemetry uplink or downlink transmission 28 or 30 to alert the medical person that the transmission is taking place.

In use, the attending medical care giver holds programmer RF head 20 against the patient's skin and over the IPG 12 to align the transceiver antennas in each as close together and as still as possible to ensure reliable telemetry transmission during the time that it takes to complete a telemetry uplink or downlink transmission 28 or 30. As described in detail in the above-incorporated '714 patent, the loading and tuning, and therefore the impedance, of the RF head telemetry antenna is affected by the proximity of the RF head telemetry antenna and the IPG telemetry antenna. Any movement can change the strength of the electromagnetic field between the two antennas during either a telemetry uplink or a downlink transmission 28 or 30 and change the strength of the signal induced by the field in the telemetry receiver antenna.

Figure 2:
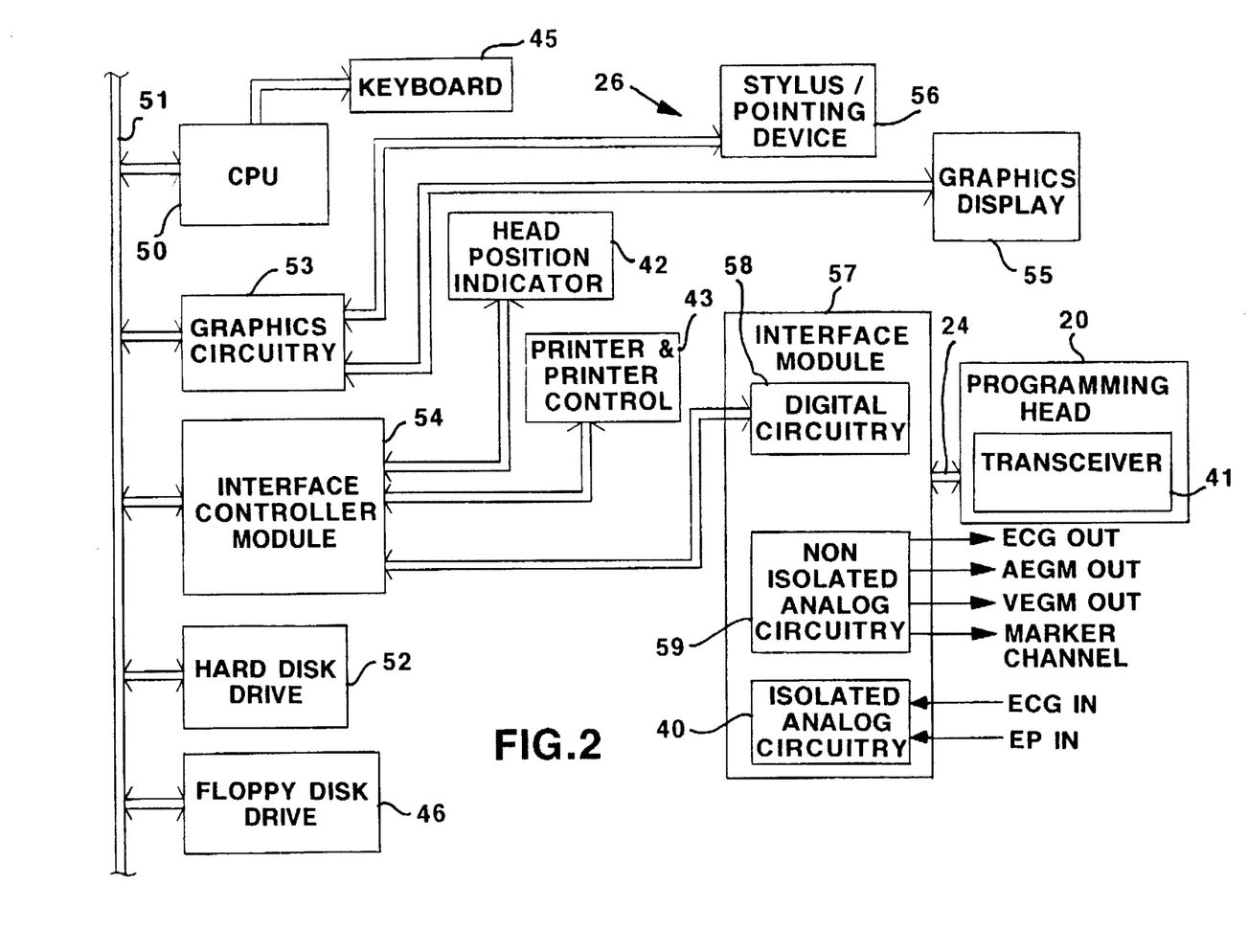
FIG. 2 is a simplified circuit block diagram of major functional blocks of the external programmer of FIG. 1.

A simplified block diagram of an exemplary programmer 26 in which the present invention may be implemented, which is preferably based upon the above-referenced MEDTRONIC® Model 9760 or 9790 programmer and depicted in detail in the above-incorporated '362 patent, is set forth in FIG. 2. Programmer 26 is a personal computer type, microprocessor-based device incorporating a central processing unit 50, which may be, for example, an Intel 80386 or 80486 or Pentium microprocessor or the like. A system bus 51 interconnects CPU 50 with a hard disk drive 52 storing operational programs and data and with a graphics circuit 53 and an interface controller module 54. A floppy disk drive 36 (or a CD ROM drive) is also coupled to bus 51 and is accessible via a disk insertion slot (not shown) within the housing of the programmer 26. Programmer 26 further comprises an interface module 57 which includes digital circuit 58, non-isolated analog circuit 59, and isolated analog circuit 40. Digital circuit 58 enables interface module 57 to communicate with interface controller module 54.

An alphanumeric keyboard 45 for entering text or numbers and other symbols is optionally provided to allow the medical person to communicate with CPU 50 in the programmer 26 as shown in the above-incorporated '362 patent. However, the primary user communication mode is through graphics display screen 55 of the well-known "touch sensitive" type controlled by graphics circuit 53 and a stylus 56 coupled thereto. Graphics display screen 55 is used to display the patient related data and menu choices and data entry fields used during telemetry uplink and downlink transmissions 28 and 30. A user of programmer 26 interacts therewith by touching stylus 56 against a selected location on screen 55 which displays the appropriate menu choices.

Graphics display 55 also displays a variety of screens of telemetered out data or real time data. Programmer 26 is also provided with a strip chart printer 63 or the like coupled to interface controller module 54 so that a hard copy of a patient's ECG, atrial and/or ventricular electrogram (AEGM, VEGM), Marker Channel or of graphics displayed on the display 55 can be generated.

As will be appreciated by those of ordinary skill in the art, it is often desirable to provide a means for programmer 26 to adapt its mode of operation depending upon the type or generation of implanted medical device to be programmed. Accordingly, it may be desirable to have an expansion cartridge containing EPROMs or the like for storing software programs to control programmer 26 to operate in a particular manner corresponding to a given type or generation or manufacturer of implantable medical device. In addition, in accordance with the present invention, it is desirable to provide the capability through the expansion cartridge or through the CD ROM or floppy disk drive 46 to expand or alter the telemetry format control or decoding software stored therein or in hard disk drive 52 as the need or opportunity to do so arises.

The programmer RF head 20 includes a transceiver 41, including a telemetry transmitter circuit, a telemetry receiver circuit, and an RF field sense circuit. The transceiver 41 is connected through cable 24 to the interface module 57.

During a telemetry uplink transmission 30, the telemetry receiver circuit in transceiver 41 is enabled. The telemetered out RF pulses of the uplink transmission 30 are detected, demodulated, decoded and applied to the digital circuit 58 to be digitized and recorded in RAM or in a hard or floppy disk or the like. The digitized data may be contemporaneously or later retrieved from memory and displayed on graphics display screen 55 or printed out for the attending medical personnel.

The analog and ventricular channel EGM signals from atrial and ventricular pace/sense electrodes may be digitized within IPG 12 and uplink telemetered to programmer 26 on receipt of a suitable INTERROGATE command. The uplink transmission 28 of the telemetered EGM signals are received in programmer RF head 20 and provided to non-isolated analog circuit 59. Non-isolated analog circuit 59, in turn, convert the digitized EGM signals to analog EGM signals (as with a digital-to-analog converter, for example) and presents these signals on output lines designated in FIG. 2 as AEGM OUT and VEGM OUT. These output lines may then be applied to a separate strip-chart recorder or the like to provide a hard-copy printout of the AEGM or VEGM signals transmitted from IPG 12 for viewing by the physician IPG 12 may also be capable of generating so-called marker codes indicative of different cardiac events that it detects. A pacemaker with Marker Channel capability is described, for example, in U.S. Pat. No. 4,374,382 to Markowitz, incorporated by reference herein in its entirety. The markers provided by IPG 12 may be received by programmer RF head 20 and presented on the MARKER CHANNEL output line from non-isolated analog circuit 59.

Isolated analog circuit 40 in interface module 57 is provided to receive external ECG and electrophysiologic (EP) stimulation pulse signals. In particular, analog circuit 40 receives ECG signals from patient skin electrodes and processes these signals before providing them to the remainder of the programmer system in a manner well known in the art. Isolated analog circuit 40 further operates to receive the EP stimulation pulses from an external EP stimulator for the purposes of non-invasive EP studies, as is also known in the art.

To initiate a telemetry uplink transmission 28, the telemetry transmitter in transceiver 41 is enabled in response to depression of the INTEROGATE push-button to generate an INTERROGATE RF pulse command that first initiates a downlink telemetry transmission 30 of a series of RF pulses. Each RF pulse of the instruction or command that is transmitted causes the IPG LC antenna circuit to ring. The train of induced voltages is detected and decoded by the receiver circuit in the IPG transceiver. After the command or instruction is decoded, the stored data to be uplink transmitted is encoded into PPM modulated RF pulses in data frames. The methods and apparatus for formatting such uplink data frames for MEDTRONIC® IPGs and other implantable medical devices are set forth in detail in the above-incorporated '404, '319 and '343 patents. The transmitter circuit in the IPG transceiver applies voltage to the IPG RF antenna causing the LC tank circuit to ring and generate the uplink RF pulses which induce signals in the RF head telemetry antenna. The induced signals are detected in the telemetry receiver circuit in transceiver 41 and applied as a pulse traion on cable 24 to interface module 57 where the frame of a series of such signals is decoded so that the data can be recorded or displayed as described above.

In the above-referenced MEDTRONIC® programmers and implantable medical devices, the frame-based telemetry format is not currently employed for downlink telemetry transmissions 30. Instead, a simpler bit stream format is employed that can be used to robustly transmit INTERROGATE commands or PROGRAM instructions under the control of CPU 50. After selection of the appropriate menu choices and during depression of an INTERROGATE or PROGRAM push-button, the CPU 50 and digital circuit 58 generate XMITTLM pulses at timed intervals the PPM position of each telemetry frame. As each downlink telemetry trigger pulse for each such frame is generated, it is applied to the telemetry transmitter circuit in the transceiver 41 which responds by applying voltage to the LC circuit of the RF head telemetry antenna.

In accordance with one aspect of the present invention, the programmer system is also adapted to generate downlink telemetry trigger pulses in accordance with other telemetry formats than the MEDTRONIC® frame-based PPM telemetry scheme, e.g., in accordance with the VITATRON® synchronous pulse PPM telemetry scheme. This may be accommodated by simply providing the format encoding software to the CPU 50 to generate the downlink telemetry trigger pulses at the appropriate times. A second aspect of the invention involves selectively changing the amplitude of the RF pulses (if necessary for a given implanted medical device) and the Q of the RF head LC tank circuit to modify the characteristics of the downlink telemetry RF pulse generated in response to the downlink telemetry trigger pulse.

FIG. 3 schematically illustrates certain components of the telemetry transmitter circuit 100 in relation to the RF head telemetry antenna 120 and the IPG antenna coil 80, tuning capacitor 82 and transceiver 84 located in IPG 12 in accordance with the present invention. The sense coil 172 and the LC tank circuit formed by tuning capacitor 164 and RF head telemetry coil 168 are shown within the programmer RF head 20. As shown in the detailed circuit of FIG. 4, the RF head telemetry coil 168 is preferably two telemetry coils 168a and 168b electrically connected in parallel and fabricated along with sense coil 172 sharing a common air core 166 in a fashion described in detail in the above-incorporated '871 and '714 patents. The tuning capacitor 164 and the parallel telemetry coils 168a and 168b are electrically connected in series between the output of the variable gain RF driver 162 and to common ground through parallel diodes 181 and 183.

The RF driver 162 comprises several stages and switched outputs and is described in greater detail below in reference to FIG. 4. It has one input terminal coupled through parallel diodes 181 and 183 to common ground and a further input terminal adapted to receive a XMITTLM pulse 160 from the interface controller module 54 (FIG. 2) for commencing generation of a downlink telemetry RF pulse. The RF driver 162 is also coupled to +12 V and −12 V terminals of regulated power supply 170 to provide drive voltages to the LC tank circuit comprising the tuning capacitor 164 and telemetry coils 168a, 168b. In the preferred embodiment, a voltage control signal NMEDORVIT is applied when the transmitter is employed in a downlink telemetry transmission 30 with a VITATRON® IPG 12 as described below.

When a XMITTLM pulse 160 is applied to an input of the RF driver 162, it causes the LC tank circuit of RF head telemetry antenna 120, comprising the tuning capacitor 164 and telemetry coil 168, to be connected in a series LC tank circuit configuration through the common ground voltage $V_L$. The RF driver 162 drives the LC tank circuit for the duration of the XMITTLM pulse 160 to generate the downlink telemetry RF burst signal in the manner described in the above-incorporated '871 patent. When this occurs, the oscillating H field 163 is generated, and an oscillating current and voltage are induced in the IPG LC tank circuit comprising IPG antenna coil 80 and tuning capacitor 82 that is detected by transceiver 84. The detected downlink telemetry transmission 30 is decoded as data to be stored in IPG memory for establishing an operating mode or a parameter value or as a command, e.g. to initiate uplink telemetry of stored data or real time EGM or to assume a temporary operating mode, etc.

When each RF telemetry pulse in a downlink telemetry transmission 30 occurs, the oscillating H field 163 is generated, and an oscillating sense voltage is also induced in the sense coil 172. The sense coil 172 is coupled to a threshold detector and amplifier 180 that is employed to generate a transmit confirmation (XMITCNF) signal when the induced sense voltage exceeds a sense threshold as described in the above-incorporated '871 patent.

The sense coil 172 is also coupled through the diodes 171 and 173 to the +12 V and −12 V terminals of regulated power supply 170. As described in the above-incorporated '714 patent, the diodes 171 and 173 are normally not conductive except when the oscillating voltage peaks induced in sense coil 172 in response to the H field exceed the approximately 0.5 V diode drop plus the supply voltage levels +12 V and −12 V, respectively. At each such occurrence, the induced peak electrical current in sense coil 172 is conducted through the sense coil to the +12 V and −12 V supply terminals. The current flow in sense coil 172 acts then to regulate the operating Q of the RF head telemetry antenna by direct loading of the magnetic, H field 163. Alternatively, it will be understood that the sense coil 172 could be connected to a sense amplifier and gain control for altering the gain of the RF driver 162 in accordance with the teachings of the above-incorporated '825 patent.

As described above, the residual energy in the RF telemetry antenna LC tank circuit causes the transmitted RF pulse to be effectively prolonged after the XMITTLM pulse 160 termination. As also described above, it may be desirable to dramatically shorten the time that it takes to complete a downlink telemetry transmission by shortening the XMITTLM pulse dramatically. For example, the frame-based PPM telemetry format normally used for uplink telemetry transmission could be employed if the XMITTLM pulse can be shortened to fit within the 32 kHz telemetry clock cycle while preserving the robust RF telemetry pulse characteristics.

In accordance with a first aspect of the present invention, this is realized by quenching or killing the trailing oscillations of the RF pulse upon termination of the XMITTLM pulse 160. This is accomplished by altering the Q of the LC tank circuit by effectively grounding both terminals of the sense coil 172 at that moment. In FIG. 3, this is accomplished by closing a pair of kill switches 191 and 193 connecting diodes 195 and 197 to common ground when the XMITTLM pulse 160 is terminated through the operation of a kill switch drive circuit 190. The kill switch drive circuit 190 responds to each XMITTLM pulse 160 by opening the kill switches 191 and 193 for the duration of the XMITTLM pulse 160 and then closing the kill switches 191 and 193 in the intervening intervals.

This dramatically lowers the antenna Q by increasing the loading of the H field during the dissipation of the residual energy in the LC tank circuit. The damped sinusoidal ringing pulse amplitudes attenuate more rapidly, ensuring that the IPG receiver will not continue to detect the transmitted RF energy following termination of the XMITTLM pulse 160. Therefore, in the frame-based PPM telemetry format, the telemetry clock frequency can be increased, resulting in a shorter clock cycle and pulse position separation without compromising the robustness of the RF telemetry pulse detection and pulse position discrimination.

Turning to the second aspect of the invention, the programmer as described to this point can also be made operable to program and interrogate implantable medical devices that employ short and discrete magnetic H field pulses, e.g. the above-described VITATRON® pacemaker IPGs. Note, that the MEDTRONIC® downlink transmission format is established involving software in the CPU 50 to operate the system in conjunction with the interface controller module 54 and the digital circuit 58. The telemetry transceiver 41 is not involved in establishing the format and can respond to any set of control signals including the XMITTLM pulse 160, regardless of when it is generated or its pulse width. Consequently, the programming and interrogation of implantable medical devices employing frame-based or non-frame-based PPM or PIM formats or PWM can be accomplished by simple software and perhaps minor hardware changes to the external programmer. The medical care giver may be instructed to key in or select the manufacturer and/or identification of the implantable medical device, and the appropriate format and mode will be selected for use in both uplink and downlink telemetry transmissions 28 and 30. The only constraint on such an approach involves any lack of compatibility with the 175 kHz carrier frequency (which has been adopted by most manufacturers as a standard In the case of VITATRON® IPGs, the downlink telemetry transmission format is a stream of short duration RF pulses that are encoded in a PPM fashion to signify binary "1"s and "0"s, the timing of which can be established in software. The discrete RF magnetic pulse that is employed in this telemetry format can be mimicked by controlling the LC tank circuit of the RF telemetry antenna 120 to emit a very short number, i.e., less than three, RF sinusoidal waves. Each full sinusoidal wave of a 175 kHz RF cycle is 5.7 μsec long. The corresponding XMITTLM pulse 170 can be reduced to 6.4 μsec to roughly time generation of a single sinusoidal wave. In accordance with this aspect of the present invention, the residual ringing of the LC tank circuit that would otherwise occur when the XMITTLM pulse terminates is suppressed by grounding the sense coil, and thereby lowering the RF head antenna Q, at termination of the XMITTLM pulse 160. Again, in this instance, the XMITTLM pulse 160 triggers the kill switch drive circuit 190 to open the kill switches 191 and 193 for the duration XMITTLM pulse 160 and to close the kill switches 191 and 193 upon its termination.

In this particular embodiment, it is also desirable to decrease the drive voltage employed in the RF driver 162. When RF telemetry pulses are generated in the MEDTRONIC® programming format, the LC tank circuit is driven at 24 volts to provide the high amplitude H field required by the characteristics of the MEDTRONIC® IPG antenna and receiver circuit. When RF telemetry pulses are generated in the VITATRON® programming format, the LC tank circuit is driven at 12 volts to produce the lower amplitude H field required by the characteristics of the VITATRON® IPG antenna and receiver circuit. The higher amplitude H field generated when 24 volts is applied would risk saturation of the VITATRON® IPG receiver circuit. The state of the NMEDORVIT signal controls the amplitude of the voltage applied to the LC tank circuit and the resulting magnetic field amplitude of the RF telemetry pulse.

FIG. 4 is a schematic circuit diagram of a preferred embodiment of implementing these principles of the present invention. The telemetry coils 168a and 168b (forming the RF head telemetry coil 168 of FIG. 3) are commonly connected at first ends to first capacitor plates of the parallel tuning capacitors 164a and 164b (forming tuning capacitor 164 of FIG. 3) to form and LC tank circuit that self resonates at 175 kHz. The second ends of the telemetry coils 168a and 168b are coupled to the circuit common ground through diode pairs 122 and 124, respectively, such that they are effectively at common ground during generation of a downlink telemetry RF pulse. The second end of telemetry coil 168a is also coupled by a feedback loop to a driver (described below) so that the LC tank circuit is driven in a self tuned regenerative feedback manner at the 175 kHz carrier frequency during a XMITTLM pulse 160 provided during a downlink telemetry transmission. The amplitude of the RF pulse is governed by an amplitude control signal designated NMEDORVIT, and the duration of the RF pulse is governed by the width of the XMITTLM pulse 160. The second plates of tuning capacitors 164a and 164b are coupled at a common node 202 to +12 V and/or −12 V terminals of the regulated power supply through FET driver stages 204 and/or 206, depending on the state of the NMEDORVIT signal.

The second ends of the telemetry coils 168a and 168b are also coupled to the RECEIVERa and RECEIVERb inputs of the uplink telemetry receiver circuit (not shown) in transceiver 41. The sense coil 172 is connected at one end to the common ground and at the second end to a resistor 126 which is in turn connected to the +12 V and −12 V terminals through diodes 171 and 173 to provide the above-described regulation of the H field. The sense coil 172 is also electrically connected at the second end to the input of the threshold detector and amplifier 180 including the comparitor stage 130 and the amplifier stage 132. The XMITCNF signal is generated when the induced sense voltage at the positive input of comparitor stage 130 exceeds the sense threshold established at the negative input terminal.

In accordance with the present invention, the second end of the sense coil is also electrically connected to the common connection of the anode and cathode of Schotke diodes 195 and 197, respectively. The cathode of diode 195 is electrically connected to FET kill switch 191, and the anode of diode 197 is electrically connected to FET kill switch 193. When FET kill switches 191 and 193 are rendered conductive at the end of the XMITTLM pulse 160, the cathode and anode of diodes 195 and 197 are coupled to common ground.

In the quiescent interval between XMITTLM pulses 160, there is no voltage applied to nor current flow through the RF telemetry antenna 120 and capacitors 164a and 164b. The XMITTLM pulse 160 is applied to the junctions of diode pair 136 and a receiver blanking (RECVRBLK) is generated and applied to the receiver circuit (not shown) to turn it off for the duration of the XMITTLM pulse 160. The XMITTLM pulse 160 is also applied to the filter 138 and then to an amplifier/inverter stage 140. The filtered and inverted XMITTLM pulse 160' is applied to FET stage 142 which produces a positive going pulse 160" that is applied to the negative input of class C amplifier stage 144 of RF driver 162. The class C amplifier stage 144 is biased between the +12 V and −12 V supply voltages, and its positive input is coupled to the diode pair 122 and to the second end of RF head telemetry coil 168a. The class C amplifier stage 144 responds to the positive going input signal corresponding (with a slight delay) to the XMITTLM pulse 160 and to the feedback signal by providing a series of drive pulses recurring at 175 kHz at its output 146 that are applied to the RF driver 162.

In the MEDTRONIC® downlink telemetry transmission mode, the XMITTLM pulse width is selected to be 350 µsec, resulting in a series of about 61 RF cycles at 175 kHz generated by ringing of the LC tank circuit during the XMITTLM pulse 160 and thereby generating about 61 drive pulses at the output 146. In the VITATRON® downlink telemetry transmission mode, the XMITTLM pulse width is selected to be about 6.4 µsec, resulting in a single 5.7 µsec drive pulse and a single corresponding RF cycle at 175 kHz generated during the XMITTLM pulse 160. As described above, the sense coil 172 is then coupled to ground through kill FET switches 191 and 193 in both cases to decrease the Q of the RF head antenna and immediately suppress residual ringing of the LC tank circuit.

In accordance with the further aspect of the preferred embodiment of the invention, one of two voltage levels is applied to the LC tank circuit depending on the state of the applied NMEDORVIT signal. When the NMEDORVIT signal state is low, for telemetry transmission with a MEDTRONIC® implantable medical device, the +12 V and −12 V terminals are successively applied at junction 202 through alternating conduction of the positive and negative FET drivers 204 and 206 which operate in an "H-drive" configuration and the grounding FET 210. In other words, in the 175 kHz positive half-cycle, the positive FET driver 204 and the grounding FET 210 are conducting or closed, and the negative FET driver 206 is non-conducting or open, thereby connecting the junction 202 of the LC tank circuit to the +12 V terminal. In the 175 kHz negative half-cycle, the positive FET driver 204 is non-conducting or open, and the negative FET driver 206 is conducting or closed, thereby connecting the junction 202 of the LC tank circuit to the −12 V terminal. In this MEDTRONIC® programmer operating mode, the about 61 RF cycles have successive +24 V peak-to-peak amplitudes, resulting in relatively high amplitude H fields during the RF pulse generation.

When the NMEDORVIT signal state is high, for telemetry with a VITATRON ® implantable medical device, the junction 202 is again coupled to +12 V terminal, but for only one RF cycle, and the junction 202 is not connected to the −12 V terminal at all. This is effected by rendering positive FET driver 204 and grounding FET 210 conducting while clamping negative FET driver 206 non-conducting.

Positive and negative push-pull FET pairs 150, 152 and 154, 156 are alternately switched into conduction and nonconduction during each 175 kHz half-cycle by the drive pulses at the output 146 of the class C amplifier stage 144. When positive push-pull FET pair 150, 152 is conducting or closed, the +12 V supply is applied to the gates of grounding FET 210, the positive FET driver 204 and a further FET 214. When negative push-pull FET pair 154, 156 is conducting or closed, the −12 V supply is applied to the gates of the negative FET driver 206 and a further FET 216. Assuming that the NMEDORVIT signal state is low, the positive FET driver 204 and the further FET 214 are rendered conductive by conduction of the positive push-pull FET pair 150, 152. The conduction of the further FET 214 applies +12 V to the gate of negative FET 154 ensuring that it and FET 156 are not switched into conduction during that half-cycle. Similarly, the negative FET driver 206 and the further FET 216 are rendered conductive by the conduction of the negative push-pull FET pair 154, 156. The conduction of the further FET 216 applies −12 V to the gate of negative FET 152 ensuring that it and FET 150 are not switched into conduction during that half-cycle.

When the NMEDORVIT signal state is high, further FETS 218 and 220 are rendered conductive. The conduction of FET 220 causes the +12 V terminal to be coupled to the gate of negative push-pull FET 154 to ensure that the negative push-pull FET pair 154, 156 are prevented from conducting. The grounding FET 210 is also rendered conductive so that +12 V is applied across resistor 208 and to the junction 202. The LC tank circuit rings, but for only about one 175 kHz cycle, because the XMITTTLM pulse 160 terminates after 6.4 μsec. Only one RF cycle is thereby produced, and its amplitude is half the amplitude of the RF pulse cycles produced in the MEDTRONIC® programming mode.

The above-describe preferred embodiment contemplates the use of the kill switches to ground the sense coil and decrease the Q of the RF head transmitting antenna at the termination of the XMITTLM pulse for all downlink telemetry transmissions. However, it will be understood that this feature of the present invention maybe employed only in selected telemetry transmissions, e.g., only when the downlink telemetry transmission is with an implantable medical device that requires the low Q antenna coil. Therefore, in this regard, it will be understood that the grounding of the sense coil at the end of the XMITTLM pulse may only be used in the case of programming the non-MEDTRONIC type implantable medical devices.

Figure 5:
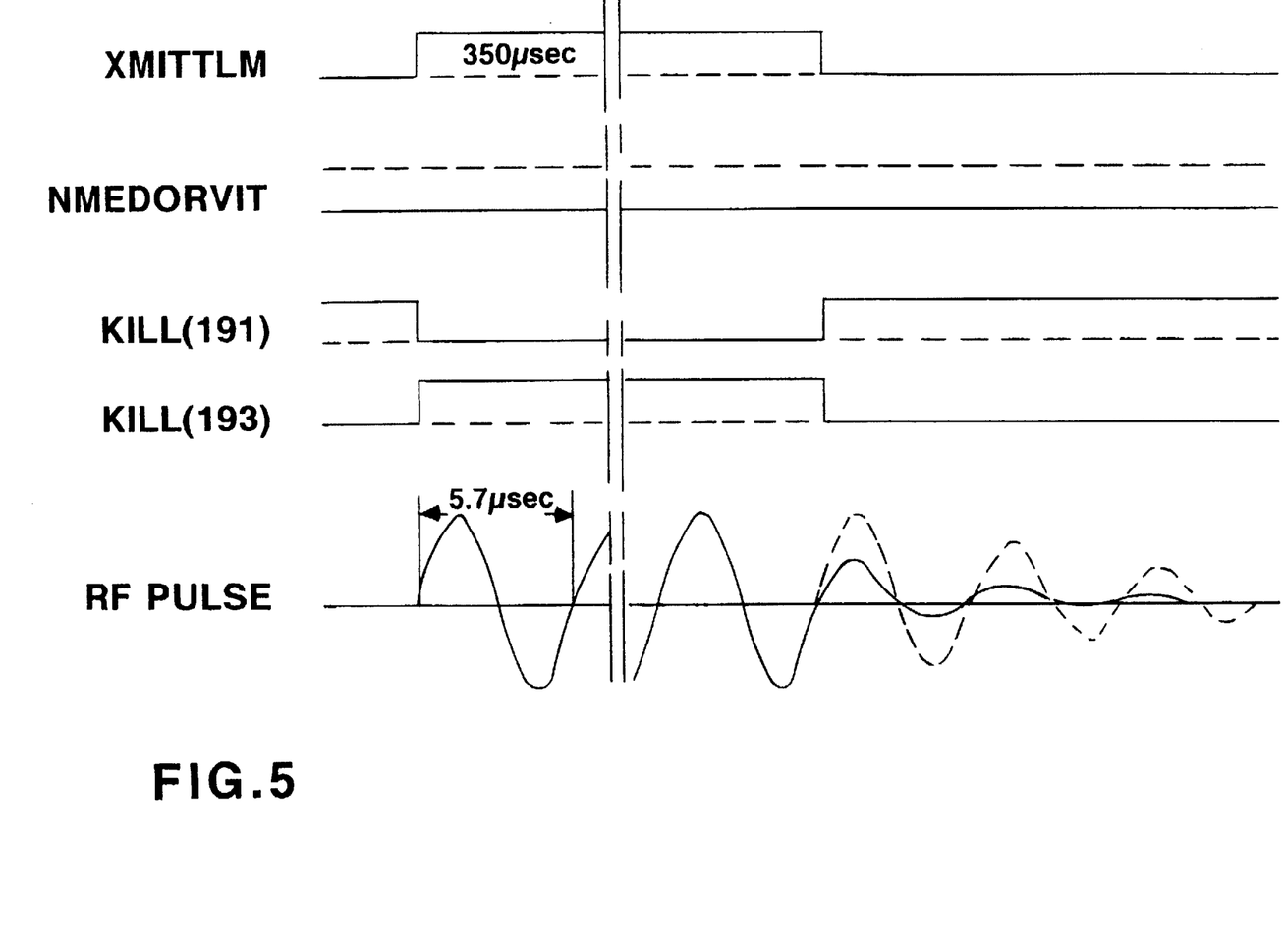
FIG. 5 is a timing diagram illustrating the generation of the RF pulses by the transmitter circuit of FIG. 4 using the sense coil to effectively lower the Q of the RF head telemetry antenna in accordance with the invention.
Figure 6:
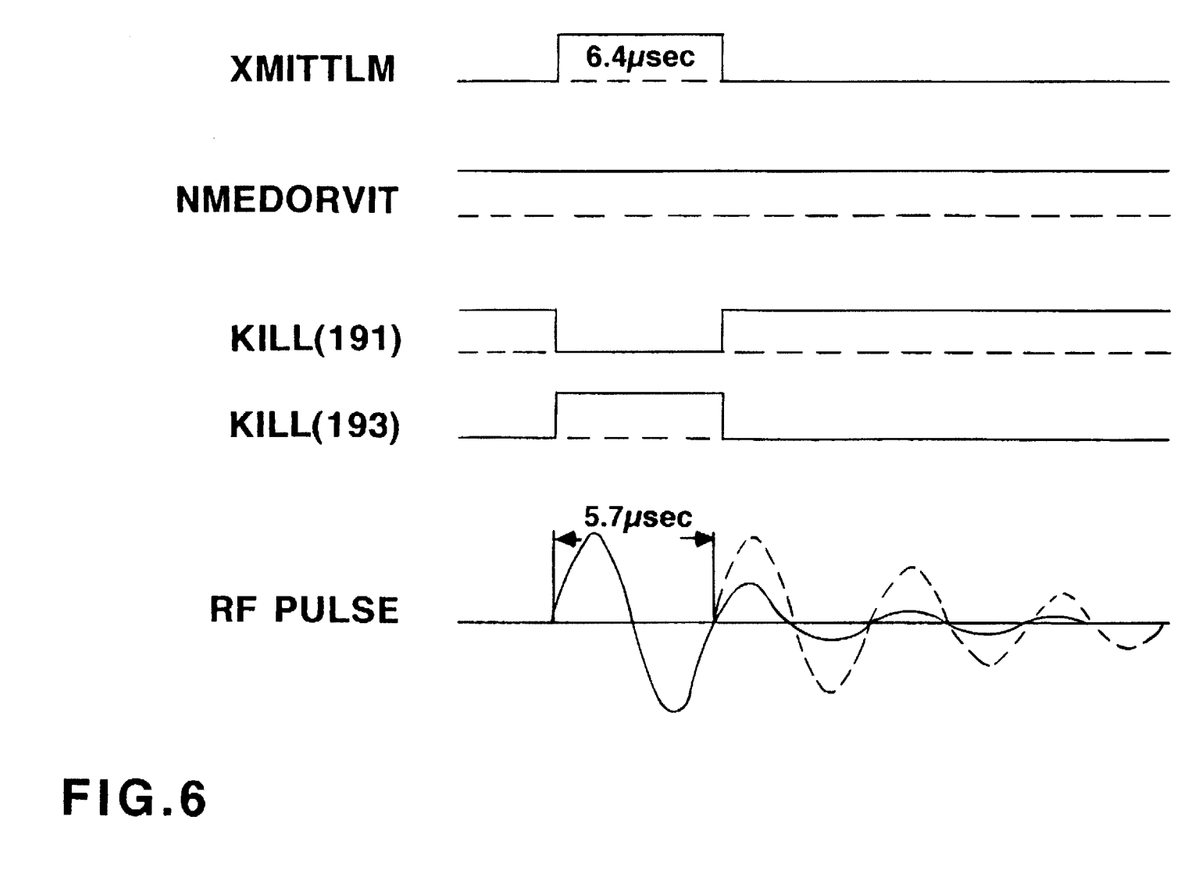
FIG. 6 is a timing diagram of the special case of the present invention allowing the RF head transmitter circuit of FIGS. 3 and 4 to be employed to generate a short duration, lower amplitude RF pulse.

FIG. 5 is a timing diagram illustrating the generation of the RF pulses by the transmitter circuit of FIG. 4 using the sense coil to effectively lower the Q of the RF head telemetry antenna in accordance with the first aspect of the invention. FIG. 6 is a timing diagram of the special case of the present invention allowing the RF head transmitter circuit of FIGS. 3 and 4 to be employed to generate a short duration, lower amplitude, RF pulse. In each case, the XMITTLM pulse 160, the state of the NMEDORVIT signal, and an open or closed representation of the sense coil kill switches 191, 193 are depicted in relation to the sinusoidal RF pulse. At the termination of the XMITTLM pulse 160, and in the absence of closure of the kill switches 191, 193, the LC tank circuit would continue to generate the damped sinusoidal, declining amplitude, RF pulse cycles depicted in broken lines. In the example of FIG. 6, this could result in erroneous detection of three or more RF pulse cycles and be rejected by the IPG receiver logic. The attenuation of the damped sinusoidal, declining amplitude, RF pulse cycles achieved by changing the RF head antenna Q through closure of the kill switches 191, 193 is illustrated in solid lines.

Specifically, representative waveforms of the original continued ringing and improved dampening of the trailing edge of the RF pulse for the single cycle VITATRON® programming mode are depicted in FIG. 6. The 6.4 μsec XMITTLM pulse is long enough to allow a single 175 kHz cycle to be generated. If the kill switches 191, 193 are not closed to ground the sense coil 172, the high Q of the RF head antenna LC tank circuit causes continued trailing edge ringing until the energy is dissipated as shown in the broken lines. However, when the sense coil 172 is grounded through the kill switches 191, 193, the trailing edge amplitude is dissipated rapidly because the Q of the RF head antenna LC tank circuit is significantly reduced by the grounded sense coil. The same effect is realized at the trailing edge of the 350 μsec XMITTLM pulse employed in the MEDTRONIC® programming mode illustrated in FIG. 5 or with any other XMITTLM pulse width.

Although not specifically shown in FIG. 6, it will be understood that the amplitude of the approximately 6.4 μsec, single carrier cycle, RF pulse depicted in FIG. 6 can be one-half the amplitude of the 350 μsec, multiple carrier cycle burst constituting the RF pulse of FIG. 5. This amplitude reduction may not always be necessary in the practice of the invention, but it can be accomplished using the NMEDOVIT signal state and the circuit as described above with reference to FIG. 4 for the specific purpose described above in detail.

Because of the invention, the same RF head antenna can be employed as a high Q, RF antenna or effectively as a low Q, RF antenna. The diminution of the residual energy ringing of the RF head LC tank circuit allows for increasing the rate of downlink telemetry or otherwise accommodating a variety of transmission rates and formats.

The preceding specific embodiments are illustrative of the practice of the invention. It is to be understood, therefore, that other expedients known to those of skill in the art or disclosed herein may be employed without departing from the invention or the scope of the appended claims. For example, the present invention is not limited to telemetry with or programming of implantable medical devices per se, but may find use in further telemetry applications between spaced RF pulse transmitters and receivers. The present invention further includes within its scope using the programmer as described hereinabove in order to program differing implantable pulse generators responsive to differing RF pulse widths, amplitudes and related characteristics.

In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures.

What is claimed is:

1. An external programmer for transmitting information-encoded, telemetry signals percutaneously from an external device to a telemetry antenna and receiver circuit in an implantable medical device in a downlink telemetry transmission, said external programmer comprising:

an RF head telemetry antenna comprising an LC tank circuit including an RF head telemetry coil and a tuning capacitor, the RF antenna having a predetermined antenna Q and adapted to be driven into oscillation by applied oscillating energy and to continue to oscillate in a series of declining amplitude oscillations after the oscillating energy is no longer applied as residually stored oscillating energy is dissipated therethrough;

means for timing the generation of a transmit telemetry pulse during the downlink telemetry transmission;

transmitter circuit means responsive to the transmit telemetry pulse for providing oscillating energy to said RF telemetry antenna during said transmit telemetry pulse whereby an RF telemetry pulse is transmitted by said RF telemetry antenna; and means operable upon the termination of said telemetry transmit pulse for reducing said antenna Q from said predetermined antenna Q and thereby attenuating the declining amplitude oscillations.

2. The programmer of claim 1, wherein said means for reducing said antenna Q further comprises:

a further coil located in a magnetic field coupling relationship with respect to said RF head telemetry coil; and means operable upon the termination of said telemetry transmit pulse for coupling said further coil to a common ground thereby reducing said antenna Q from said predetermined antenna Q through loading of the magnetic field and thereby attenuating the declining amplitude oscillations.

3. The programmer of claim 2, wherein said further coil further comprises a sense coil for sensing the generation of the magnetic field by the antenna coil during said transmit telemetry pulse.

4. The programmer of claim 2, wherein said further coil further comprises:

a sense coil for sensing the generation of the magnetic field by the antenna coil during said transmit telemetry pulse and generating a sense voltage in response thereto; and means for comparing the amplitude of the sense voltage to a reference voltage and for causing current to flow in said sense coil when said sense voltage amplitude exceeds said reference voltage amplitude to thereby directly load the magnetic field generated by said antenna coil and regulate the amplitude of the RF telemetry pulse during said transmit telemetry pulse.

5. A method for transmitting information-encoded, telemetry signals percutaneously between an implanted medical device and an external device as telemetry RF pulses employing an RF head telemetry antenna comprising an LC tank circuit including an RF head telemetry coil and a tuning capacitor, the RF head telemetry antenna having a predetermined antenna Q and adapted to be driven into oscillation by applied oscillating energy and to continue to oscillate in a series of declining amplitude oscillations after the oscillating energy is no longer applied as residually stored oscillating energy is dissipated therethrough, the method comprising the steps of:

providing a transmit telemetry pulse for establishing a pulse width of the telemetry RF pulse;

providing oscillating energy to said RF telemetry antenna during said transmit telemetry pulse, whereby an RF telemetry pulse is transmitted by said RF telemetry antenna; and upon the termination of said telemetry transmit pulse, reducing said antenna Q from said predetermined antenna Q and thereby attenuating the declining amplitude oscillations.

6. The method of claim 5, wherein said step of reducing said antenna Q further comprises the steps of:

locating a further coil in a magnetic field coupling relationship with respect to said RF head telemetry coil; and upon the termination of said telemetry transmit pulse, coupling said further coil to a common ground thereby reducing said antenna Q from said predetermined antenna Q through loading of the magnetic field and thereby attenuating the declining amplitude oscillations.

7. The method of claim 6, wherein said further coil further comprises a sense coil for sensing the generation of the magnetic field by the antenna coil during said transmit telemetry pulse.

8. The method of claim 6, wherein said further coil further comprises a sense coil for sensing the generation of the magnetic field by the antenna coil during said transmit telemetry pulse and generating a sense voltage in response thereto, and further comprising the step of:

comparing the amplitude of the sense voltage to a reference voltage and causing current to flow in said sense coil when said sense voltage amplitude exceeds said reference voltage amplitude to thereby directly load the magnetic field generated by said antenna coil and regulate the amplitude of the RF telemetry pulse during said transmit telemetry pulse.

9. A telemetry programmer for transmitting information-encoded, telemetry signals percutaneously to an implanted medical device as telemetry RF pulses comprising:

an RF head telemetry antenna comprising an LC tank circuit including an RF head telemetry coil and a tuning capacitor, the RF head telemetry antenna having a predetermined antenna Q and adapted to be driven into oscillation by applied oscillating energy and to continue to oscillate in a series of declining amplitude oscillations after the oscillating energy is no longer applied as residually stored oscillating energy is dissipated therethrough;

means for providing a transmit telemetry pulse for establishing a pulse width of the telemetry RF pulse;

a telemetry transmitter for providing oscillating energy to said RF telemetry antenna during said transmit telemetry pulse, whereby an RF telemetry pulse is transmitted by said RF telemetry antenna; and means operable upon the termination of said telemetry transmit pulse for reducing said antenna Q from said predetermined antenna Q and thereby attenuating the declining amplitude oscillations.

10. The programmer of claim 9, wherein said means for reducing said antenna Q further comprises:

a further coil located in a magnetic field coupling relationship with respect to said RF head telemetry coil; and means operable upon the termination of said telemetry transmit pulse for coupling said further coil to a common ground thereby reducing said antenna Q from said predetermined antenna Q through loading of the magnetic field and thereby attenuating the declining amplitude oscillations.

11. The programmer of claim 10, wherein said further coil further comprises a sense coil for sensing the generation of the magnetic field by the antenna coil during said transmit telemetry pulse.

12. The programmer of claim 10, wherein said further coil further comprises:

a sense coil for sensing the generation of the magnetic field by the antenna coil during said transmit telemetry pulse and generating a sense voltage in response thereto; and means for comparing the amplitude of the sense voltage to a reference voltage and for causing current to flow in said sense coil when said sense voltage amplitude exceeds said reference voltage amplitude to thereby directly load the magnetic field generated by said antenna coil and regulate the amplitude of the RF telemetry pulse during said transmit telemetry pulse.

13. A medical device system comprising:

an implantable medical system adapted to be implanted in a patient and further comprising a medical device telemetry receiver for receiving telemetry RF pulses; and an external programmer for transmitting information-encoded, telemetry signals percutaneously between an implanted medical device and an external device as telemetry RF pulses further comprising:

an RF head telemetry antenna comprising an LC tank circuit including an RF head telemetry coil and a tuning capacitor, the RF head telemetry antenna having a predetermined antenna Q and adapted to be driven into oscillation by applied oscillating energy and to continue to oscillate in a series of declining amplitude oscillations after the oscillating energy is no longer applied as residually stored oscillating energy is dissipated therethrough;

means for providing a transmit telemetry pulse for establishing a pulse width of the telemetry RF pulse;

a telemetry transmitter for providing oscillating energy to said RF telemetry antenna during said transmit telemetry pulse, whereby an RF telemetry pulse is transmitted by said RF telemetry antenna;

a further coil located in a magnetic field coupling relationship with respect to said RF head telemetry antenna; and means operable upon the termination of said telemetry transmit pulse for coupling said further coil to a common ground thereby reducing said antenna Q from said predetermined antenna Q and thereby attenuating the declining amplitude oscillations.

14. The system of claim 13, wherein said further coil further comprises a sense coil for sensing the generation of the magnetic field by the antenna coil during said transmit telemetry pulse.

15. The system of claim 13, wherein said further coil further comprises:

a sense coil for sensing the generation of the magnetic field by the antenna coil during said transmit telemetry pulse and generating a sense voltage in response thereto; and means for comparing the amplitude of the sense voltage to a reference voltage and for causing current to flow in said sense coil when said sense voltage amplitude exceeds said reference voltage amplitude to thereby directly load the magnetic field generated by said antenna coil and regulate the amplitude of the RF telemetry pulse during said transmit telemetry pulse.

16. In a medical system for transmitting information-encoded, telemetry signals percutaneously between an implanted medical device and an external device as telemetry RF pulses employing an RF head telemetry antenna comprising an LC tank circuit including an RF head telemetry coil and a tuning capacitor, the RF head telemetry antenna having a predetermined antenna Q and adapted to be driven into oscillation and to continue to oscillate in a series of declining amplitude oscillations after the oscillating energy is no longer applied as residually stored oscillating energy is dissipated therethrough, a method of altering the RF head antenna to transmit such telemetry RF pulses with high Q or low Q comprising the steps of:

providing a transmit telemetry pulse for establishing a pulse width of the telemetry RF pulse;

providing oscillating energy to said RF telemetry antenna during said transmit telemetry pulse, whereby an RF telemetry pulse is transmitted by said RF telemetry antenna; and selectively varying the RF telemetry antenna Q from a high Q to a relatively lower Q and thereby attenuating the declining amplitude oscillations at the end of the transmit telemetry pulse.

17. The method of claim 16, wherein said step of selectively varying said antenna Q further comprises the steps of:

locating a further coil in a magnetic field coupling relationship with respect to said RF head telemetry coil; and upon the termination of said telemetry transmit pulse, coupling said further coil to a common ground thereby reducing said antenna Q from said predetermined antenna Q through loading of the magnetic field and thereby attenuating the declining amplitude oscillations.

18. The method of claim 17, wherein said further coil further comprises a sense coil for sensing the generation of the magnetic field by the antenna coil during said transmit telemetry pulse.

19. The method of claim 17, wherein said further coil further comprises a sense coil for sensing the generation of the magnetic field by the antenna coil during said transmit telemetry pulse and generating a sense voltage in response thereto, and further comprising the step of:

comparing the amplitude of the sense voltage to a reference voltage and causing current to flow in said sense coil when said sense voltage amplitude exceeds said reference voltage amplitude to thereby directly load the magnetic field generated by said antenna coil and regulate the amplitude of the RF telemetry pulse during said transmit telemetry pulse.

20. The method of claim 16 wherein the step of providing a transmit telemetry pulse for establishing a pulse width of the telemetry RF pulse further comprises establishing a pulse width allowing the a single cycle of the RF telemetry pulse.

* * * * *